United States Patent [19]
Radd et al.

[11] 3,975,253
[45] Aug. 17, 1976

[54] PROCESS CHANGE SENSOR

[75] Inventors: Frederick J. Radd; Louis H. Wolfe; Donald H. Oertle, all of Ponca City, Okla.

[73] Assignee: Continental Oil Company, Ponca City, Okla.

[22] Filed: Mar. 26, 1975

[21] Appl. No.: 562,281

[52] U.S. Cl. .......................................... 204/195 R
[51] Int. Cl.² ........................................ G01N 27/46
[58] Field of Search .......... 204/195 R, 195 P, 195 F

[56] References Cited
UNITED STATES PATENTS

| | | | |
|---|---|---|---|
| 1,474,151 | 11/1923 | Keeler | 204/195 R |
| 2,414,411 | 1/1947 | Marks | 204/195 R |
| 2,684,938 | 7/1954 | Mantzell | 204/195 F |
| 3,498,900 | 3/1970 | Banks et al. | 204/195 R |

*Primary Examiner*—T. Tung
*Attorney, Agent, or Firm*—F. Lindsey Scott

[57] ABSTRACT

A process change sensor comprising a tubing means, a first electrode positioned at one end of the tubing means for contact with a process medium, a second, permeable electrode positioned inwardly in the tubing means from said first electrode, a porous body separating said second electrode from said first electrode, means for supplying electrolyte through said tubing means to said second electrode whereby said supplied electrolyte can flow through said porous body to said first electrode, and means for measuring the change in EMF between said first and second electrodes as a result of changes in the process medium at said first electrode.

5 Claims, 10 Drawing Figures

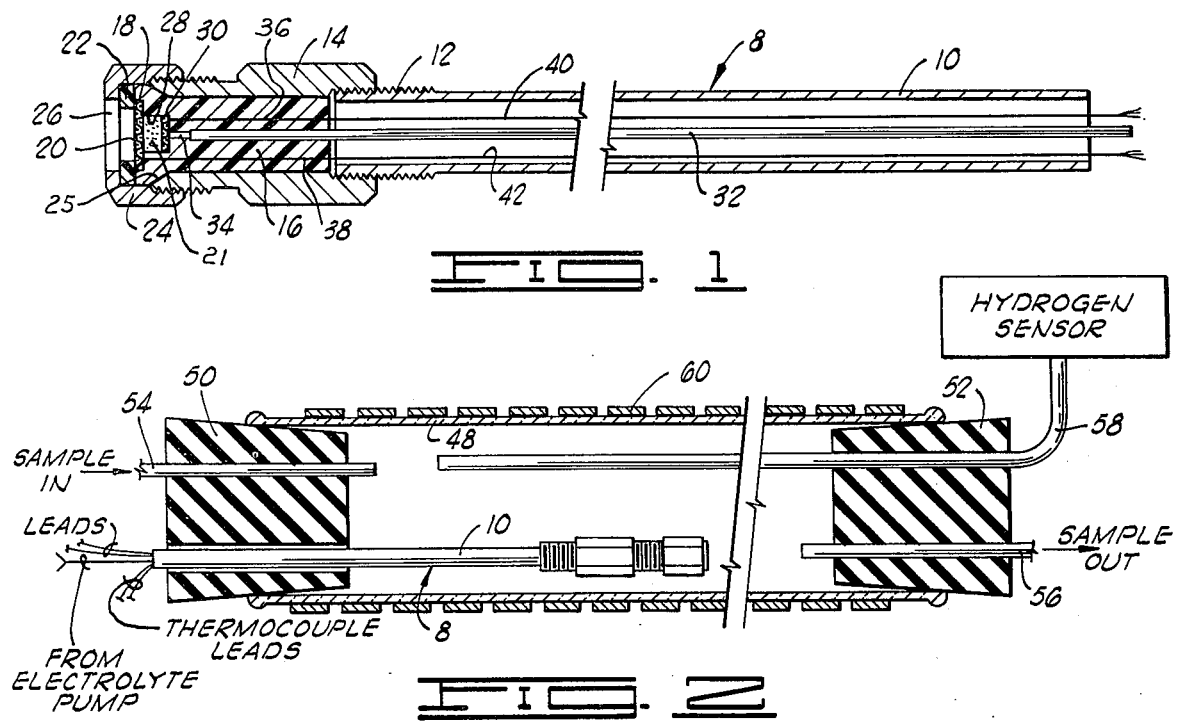
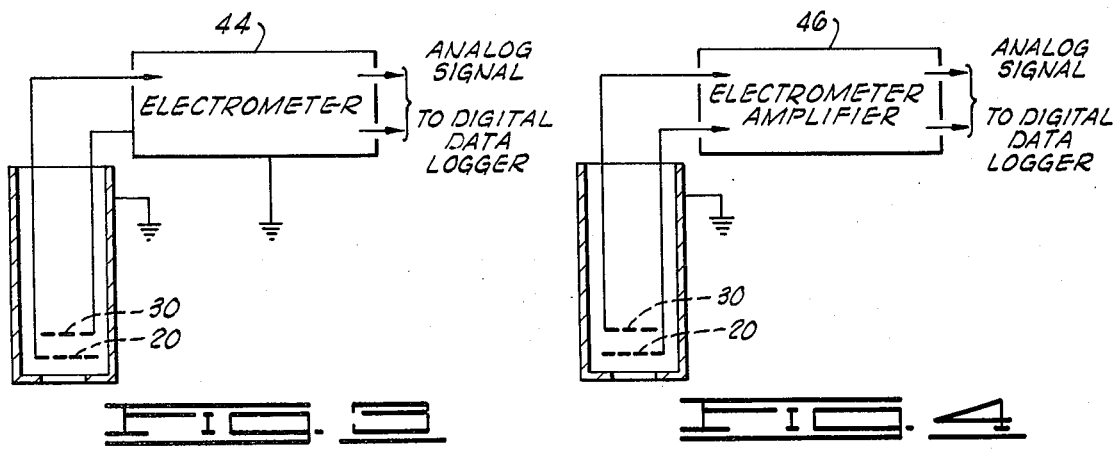
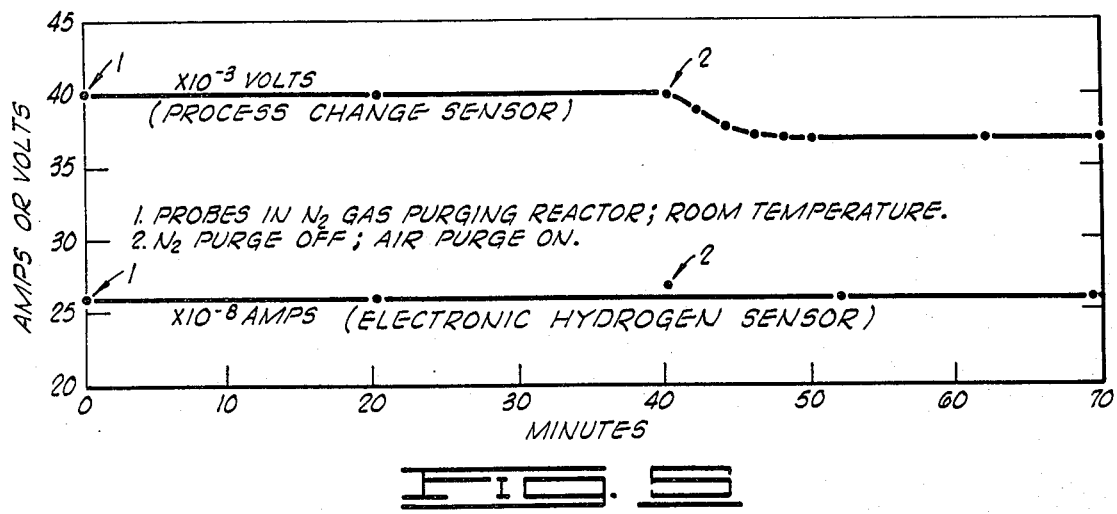

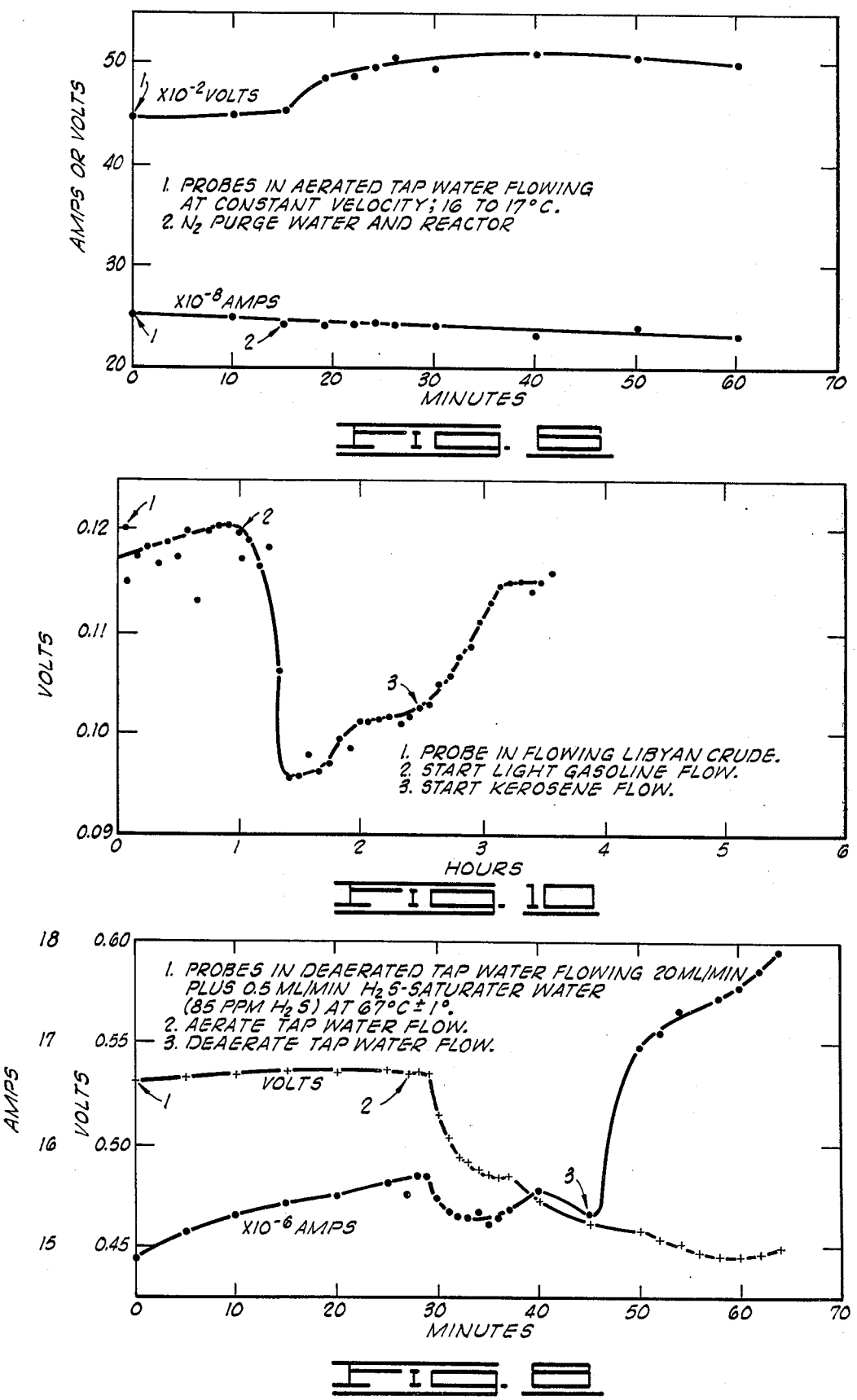

PROCESS CHANGE SENSOR

BACKGROUND OF THE INVENTION

1. Field of the Invention

This invention relates to probes and sensing devices for sensing EMF changes in a process environment, and more particularly, to probes and sensors of the type which contain a reference electrode and a second electrode spaced therefrom, and which detect or determine changes in a property of a process medium adjacent to at least one of the electrodes.

2. Brief Description of the Prior Art

A number of types of probes and sensor devices have been proposed for electronically monitoring or sensing changes in process conditions and parameters. These have been used for various purposes, including, for example, measuring changes in the oxygen content of a solution, determining hydrogen content of high-temperature fluids and monitoring corrosion in a system. One general type of probe used for these purposes includes a reference electrode and a second electrode, sometimes called a working electrode, both positioned in spaced relation in a housing of some type, and connected to a potential-measuring device. Change in the EMF across the electrodes is indicative of a change in a particular process condition monitored.

A number of criteria have been used to evaluate the effectiveness of such probes or sensor devices, including the speed of response (how quickly the process change is sensed and indicated), the cost or expense of constructing the probe or sensor, its mechanical durability, and its universality (ability to be used, for example, in both the gas, liquid, or mixed phase systems). Some types of probes previously used have been relatively narrow in their applicability and usefulness, and others have had a slow or delayed response time which is acceptable in some usage, but unsatisfactory in others. One type of electronic hydrogen sensor now in use for corrosion monitoring works well in selectively detecting process changes which cause corrosion. When a film inhibiting the sensitivity of the probe forms on the steel hydrogen diffusion tube of the sensor, the detection is delayed in its response to process changes which result in corrosion. This represents corrosion to be experienced by the process vessel, but does not serve as an early warning of possible corrosion.

Many of the types of electrodes previously in use are expensively constructed, employing platinum tubes and wires, and/or expensive chemical packings, or costly catalytic coatings on noble metals.

Examples of some of the dual electrode type probes or sensing devices recently proposed and patented include those shown in U.S. Pat. No. 3,657,096 to Proctor; U.S. Pat. No. 3,510,420 to Mills; U.S. Pat. No. 3,647,641 to Grubb et al.; U.S. Pat. No. 3,661,749 to Richardson; U.S. Pat. No. 3,649,473 to Holden et al.; U.S. Pat. No. 3,328,277 to Solomons et al., and U.S. Pat. No. 2,913,386 to Clark.

BRIEF DESCRIPTION OF THE PRESENT INVENTION

The present invention provides a new process change sensor which can be used for process and flow control studies. The sensor has a very fast response time and is effective in its monitoring and sensing functions in both the liquid and gas phase. The sensor is quite usefully employed in combination with an electronic hydrogen sensor for detecting and defining process, corrosion and metallurgical variables of the system under study.

Broadly described, the process change sensor of the invention comprises a tubing means, a first permeable electrode positioned at one end of the tubing means for contact with the process medium, a second permeable electrode positioned inwardly in the tubing means from said first electrode, a porous body separating said second electrode from said first electrode, means for supplying electrolyte through said tubing means to said second electrode whereby said supplied electrolyte can flow through said porous body to said first electrode, and means for measuring the change in the EMF between said first and second electrodes as a result of changes in the process medium at said first electrode. In another aspect, the invention contemplates a bi-sensor system and method in which the process change sensor described is utilized in combination with an electronic hydrogen sensor for monitoring changes in the process, corrosion and metallurgical characteristics of a process environment.

An important object of the present invention is to provide a process change sensor of wide utility for indicating changes and variations in process conditions and parameters in such locations as chemical plants, pipelines, paper pulp plants, chemical ships or tankers and many other locations where it is desirable to be aware of changes in the chemical and/or physical character of the system in use.

Another object of the invention is to provide an inexpensive, durable and sturdily constructed process change sensor which can be utilized to monitor changes occurring either in the gas or liquid phase in a process environment.

Another object of the invention is to provide a process change sensor which can respond rapidly to changes in the conditions occurring in a process environment, including changes in the process which may cause corrosion of metals in that environment.

Another object of the invention is to provide a process change sensor which is quite rapid in its response, and will generally perceptibly indicate a change in process conditions within a period of two to thirty seconds after such change occurs in the vicinity of the sensor.

A further object of the invention is to provide a bi-sensor system which includes an electronic hydrogen probe and the quick response process change sensor used in combination to identify and isolate process events which may cause metallurgical changes as a result of corrosion, including identification and resolution of process events which cause immediate corrosion, as contrasted with those which cause delayed corrosion.

Another object is to provide a method of using the described bi-sensor system.

Additional objects and advantages of the invention will become apparent as the following detailed description of preferred embodiments of the invention is read in conjunction with the accompanying drawings which illustrate the invention.

BROAD DESCRIPTION OF THE DRAWINGS

FIG. 1 is a sectional view along the longitudinal axis of the process change sensor of the present invention.

FIG. 2 is a sectional view along the longitudinal axis of a test apparatus utilized in testing the process change sensor of the invention.

FIG. 3 is a schematic illustration of electronic circuitry used in conjunction with the process change sensor of the invention.

FIG. 4 is a schematic illustration of a different embodiment of an electronic circuit used in conjunction with the process change sensor.

FIGS. 5–10 are graphs plotting the EMF across the electrodes of the process control sensor, and the ion pump current of the hydrogen sensor, against time for a series of tests made utilizing the sensor devices.

DETAILED DESCRIPTION OF PREFERRED EMBODIMENTS OF THE INVENTION

Figure 7:
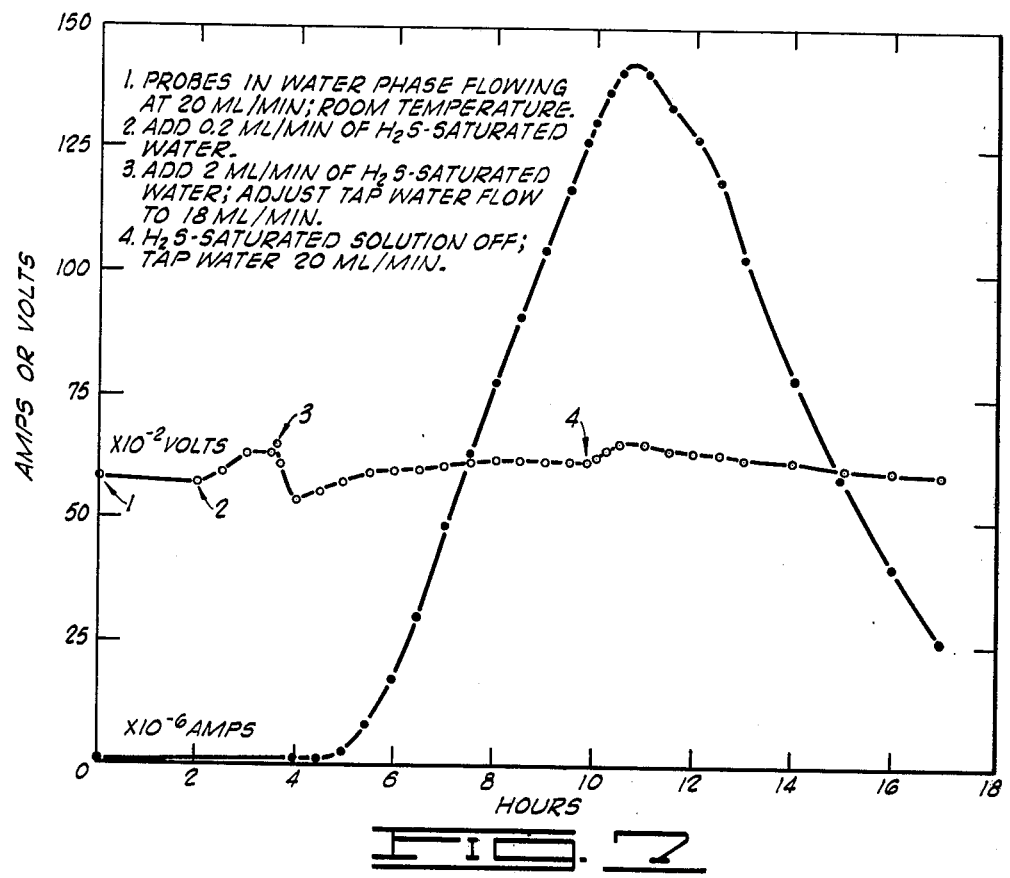

Referring to FIG. 1 of the drawings, the process change sensor 8 of the invention comprises tubing means which includes an elongated tube 10 which carries external threads 12 adjacent one end thereof. The tube 10 is screwed into housing means which includes a fitting 14 which has positioned internally therein, an insulating seal fixture 16, which in one form, can suitably be made of a polyfluoroethylene synthetic resin. The insulating seal fixture 16 has a bore 18 at one end thereof which receives a platinum gauze working electrode 20. The working electrode 20 is held in place by a synthetic resin washer 22 which abuts the end of the insulating seal fixture 16 and is retained in position by a metallic cap 24 which is threaded on the opposite end of the fitting 14 from the female end thereof which receives the tube 10. The cap 24 compresses the insulating washer 22 and the fixture 16 against taper 25 of fitting 14 to form a wedge-type seal. The cap 24 is provided with an opening 26 in the end thereof to permit process fluids to contact the platinum gauze working electrode 20.

A counterbore 28 projects inwardly in the fixture 16 from the bore 18 and receives a platinum gauze reference electrode 30. The platinum gauze reference electrode 30 is separated from the working electrode 20 by a fritted glass plug 21 which is porous to a reference electrolyte as hereinafter described. An elongated electrolyte delivery tube 32 which can be constructed of glass, synthetic resin or metal projects into, and is sealingly attached to, the fixture 16 along the central axis thereof, and terminates with one end spaced from the reference electrode 30. A small electrolyte passageway 34 is provided for conveying reference electrolyte from the tube 32 to the reference electrode 30.

A platinum lead 36 is sealingly threaded into the fixture 16 to a point of securement at one end thereof to the reference electrode 30, and a second platinum lead 38 is sealingly threaded into the fixture to a point of securement to the working electrode 20. The fixture 16 is, of course, constructed of an electrically non-conductive or insulating material, and insulates the platinum leads 36 and 38 from each other. Copper wires 40 and 42 are soldered to the exposed outer ends of the leads 36 and 38 and project through the tube 10 and out of the open end thereof remote from the fitting 14 for connection to electrical circuitry as hereinafter described. It should be pointed out that other metals than the preferred platinum can be used in the construction of the electrodes 20 and 30, and other metallic wires than copper wires can be used for connection to the short electrode lead wires 36 and 38.

In the use of the process change sensor 8 for monitoring a change in a process condition or parameter, the end of the sensor which carries the reference electrode 30 and the working electrode 20 is inserted through a suitable opening in a housing or pipeline in which the process is carried out, and a packing gland of suitable construction is employed to provide a pressure seal around the tube 10 when the sensor is in place. A suitable electrolyte pump (not shown) is then employed for pumping a reference electrolyte through the internal tubing 32, through the passageway 34 and into contact with the reference electrode 30. The reference electrode 30 is, of course, porous, and the reference electrolyte can then pass through the fritted glass plug 21 and into contact with the working electrode 20 and into a position to co-mingle with the process fluid to which the working electrode 20 is exposed through the opening 26. A reference electrolyte pump which has been found to be especially suitable for use with the process change sensor of the invention is a gas operated pump sold under the name "Oscillimatic Chemical Injector" by the Williams Instrument Company, Inc., San Fernando, Cal. This pump has a wide range of liquid delivery of from about 16 to about 400 ml/hr. against 5,000 psi. It will operate several days on a bottle of nitrogen with a very accurate delivery, and it can also be operated from available instrument air supplies in refineries.

Two embodiments of electrical circuitry utilized as a part of the process change sensor 8 of the invention to provide a read-out indicative of process changes are illustrated in FIGS. 3 and 4. In the embodiment illustrated in FIG. 3, the process change sensor electrodes 20 and 30 are connected to the single ended and ground input of an electrometer 44. An electrometer found to be very suitable is the Model 610A Electrometer manufactured by Keithley Instruments, Inc., of Cleveland, Ohio, and having $10^{14}$ ohms or above input impedance, which can conveniently be used with the voltage set on the 10 volt range. The output from the electrometer is connected to the 2 volt input of a digital data logger used for recording the output from the process change sensor to the nearest 0.001 volt. The digital data logger can also be used to record the output from an electronic hydrogen sensor useful in combination with the process change sensor as hereinafter described, and from a thermocouple inserted in the tube 10 of the process change sensor in a manner and for a purpose hereinafter described. As the sensor electrodes must have a constant, high impedance load across them, the electrometer 44 is used between the process change sensor 8 and the digital data logger. Because of the constant high impedance load, the electrometer is desirably set at a range such that the digital data logger will record a ± 1 volt output for a ± 1 volt input from the process change sensor electrode, regardless of the data logger sampling time or rate. In the embodiment of the circuitry illustrated in FIG. 3, the lead from the reference electrode 30 is connected to the ground terminal of the electrometer 44, and the working electrode 20 is connected to the input terminal of the electrometer.

Another and preferred electronic read-out circuit utilized with the process change sensor of the invention is illustrated in FIG. 4. In this circuit, an electrometer solid state operational amplifier 46 with floating inputs is employed, so that operation can be carried out with both electrodes of the process change sensor 8 floating above ground.

As previously pointed out herein, one aspect of the present invention is the utilization of the process change sensor 8 illustrated in FIG. 1, and hereinbefore described, in combination with an electronic hydrogen sensor of a type previously known and utilized for monitoring corrosion, metallurgical and/or process characteristics of a system. The electronic hydrogen sensor includes an elongated steel tube which constitutes a metallic membrane through which atomic hydrogen diffuses as corrosion occurs at the surface of the tube. The tube is closed at one end, and the atomic hydrogen which diffuses through the tube to the interior thereof is drawn into an ion pump and trapped internally. The pump rate and, correlatively, the ion pump current, provides an indication of the amount of atomic hydrogen diffusing through the tube, and thus is a measure of corrosion rate. Stated differently, as the rate of corrosion increases, a greater quantity of atomic hydrogen diffuses through the tube, the pressure in the tube increases, and the ion pump current increases so that a direct linear relationship exists between the amount of gas being pumped by the ion pump and the ion pump current. A device of this type is described in *Vacuum Technology*, A. Guthrie, J. Wiley and Sons, New York, N.Y., 1963, which is incorporated herein by reference.

For the purpose of testing the process change sensor, as well as the bi-sensor system utilizing an electronic hydrogen sensor in conjunction with the process change sensor, a laboratory flow-through reactor was designed and had the appearance illustrated in FIG. 2. The reactor included a Pyrex tube 48 about 16 inches long, about 1½ inch in inside diameter, and closed at opposite ends with rubber stoppers 50 and 52. The process change sensor 8 was projected through a hole in one of the stoppers at one end of the tube 48 and an iron-constantan thermocouple was inserted into the extension tube 10 of the sensor so that the temperature of the sensor could be detected and recorded continuously. A pair of tubes 54 and 56 were provided through each of the stoppers 50 and 52 at opposite ends of the reactor for conveying a process fluid into and through the reactor. In the rubber stopper 52 at one end of the tube 48, a steel tube 58 constituting a part of an electronic hydrogen sensor device, and connected to an ion pump in the manner hereinbefore described, was extended through the stopper into the interior of the Pyrex tube. The Pyrex tube 48 of the reactor was wrapped with a 288 watt heater tape 60, and was insulated with glass wool and aluminum foil (not shown). The current to the heating tape was controlled with a standard 8 amp variable auto-transformer.

In a series of laboratory experiments, a selected electrolyte was pumped through the internal tubing 32 and passageway 34 to the reference electrode 30. The electrolyte then diffused through the porous plug 21 to the working electrode 20. Various types of liquid and gaseous fluids were then charged to the reactor via the sample inlet tube 54, and were discharged from the reactor through the sample outlet tube 56.

The following examples illustrate the use of the process change sensor of the invention, both alone as a sensitive indicator of changes in process conditions and parameters, and in conjunction with an electronic hydrogen sensor in a bi-sensor system used to detect metallurgical corrosion and/or process changes, in addition to other changes, or in conjunction with other instruments. In Example 8, the preferred electrical circuitry illustrated in FIG. 4 was employed. In all other examples, the circuitry shown in FIG. 3 was used.

EXAMPLE 1

A reference electrolyte consisting of a 1.0 weight percent ammonium hydroxide-deionized water electrolyte was pumped to the process change sensor via the internal tubing 32 at a rate of about 20 ml/hr. The reactor tube 48 was tipped to be about 5° from the horizontal so that the electrolyte would drain from the reactor. Continuous measurements were taken of the potential across the reference and working electrodes of the process change sensor, and the ion current of the electronic hydrogen sensor was concurrently continuously monitored. The test was carried out at ambient temperature.

Initially, the Pyrex tube 48 was purged with nitrogen gas. When the potential across the electrodes of the process sensor appeared to be stabilized, the nitrogen purge gas was turned off, and air was charged to the reactor through the tubing 54. The response of the process change sensor 8 and the electronic hydrogen sensor to the change occurring in the gaseous phase when nitrogen was followed by air is shown in FIG. 5 of the drawings. This discrimination ability of the process change sensor 8 is clearly apparent, since an appreciable differential signal was obtained. The electronic hydrogen sensor did not respond to the change in the gas phase because there was not an appreciable difference in corrosion.

EXAMPLE 2

Aerated tap water was caused to flow through the Pyrex tube 48 at a temperature of about 17°C at a constant velocity. Upon the attainment of stability of the potential and current readouts from the process change sensor and the electronic hydrogen sensor, the water charged to the reactor was deaerated by purging with nitrogen, and the reactor was purged with nitrogen. As shown in FIG. 6, the process change sensor voltage changed significantly when the flowing tap water in the reactor was replaced by deaerated water. Again, as in Example 1, the electronic hydrogen sensor did not sense a change in process conditions because the corrosion rate did not change significantly.

EXAMPLE 3

At the outset of this experiment, flowing tap water was first passed through the reactor at a rate of 20 ml/min. and at room temperature. Periodically, various amounts of hydrogen sulfide-saturated tap water were added to the flowing water. Ultimately, the hydrogen sulfide-saturated water addition was stopped, and the unaltered tap water flow was resumed.

The responses of the process change sensor and the electronic hydrogen sensor are shown in FIG. 7. It will be noted in referring to this figure of the drawings that the response of the process change sensor to the additions of hydrogen sulfide was much more rapid than that of the electronic hydrogen sensor, and that the process change sensor provided much faster event indications. Although the signal level changes for the process change sensor were not large in magnitude, all of the changes resulting from the addition of the hydrogen sulfide were clearly indicated.

At the start of the additions of hydrogen sulfide, the steel tube 58 of the electronic hydrogen sensor was a rusty red color. The ion pump current readings evidenced little hydrogen diffusion as a result of corrosion until the tube 58 became black at the time the $H_2S$ had completed its reaction with the oxide and had started to react with the probe metal.

Several hours were needed for the electronic hydrogen sensor to respond, and although the response was large, it was not clearly connected by time to the time of process change events resulting from hydrogen sulfide addition. This was, of course, due to the delayed response to process changes caused by varying surface conditions, such as the rust on the hydrogen sensor probe.

EXAMPLE 4

In this experiment, both the process change sensor 8 and the electronic hydrogen sensor were located in the vapor phase above a flowing liquid. Initially, tap water was flowed through the reactor at a rate of 20 ml/min. at room temperature. This was followed after a time interval by water to which hydrochloric acid had been added. This was, in turn, followed after a time interval, by the addition of hydrogen sulfide to the hydrochloric acid-containing water. Finally, both the hydrochloric acid addition and the hydrogen sulfide addition were terminated, and tap water flow was resumed. The results of this test are shown in Table 1.

TABLE I

| Time, min. | Sensor Response | |
|---|---|---|
| | Process Change Sensor, Volts ×10⁻¹ | Electronic Hydrogen Sensor, Amps ×10⁻⁶ |
| 0[1] | 0.62 | 0.40 |
| 15 | 0.60 | 0.40 |
| 31[2] | 0.58 | 0.40 |
| 36 | 0.55 | 0.40 |
| 45 | 0.63 | — |
| 59 | 0.71 | — |
| 77 | 0.77 | 0.41 |
| 105 | 0.90 | 0.41 |
| 135[3] | 0.99 | 0.41 |
| 142 | 0.88 | 0.42 |
| 144 | 2.70 | 0.41 |
| 150[4] | 2.75 | — |
| 165 | 2.50 | — |
| 180 | 2.32 | 0.41 |
| 212 | 2.22 | — |
| 230[5] | 2.31 | — |
| 235 | 1.30 | — |
| 240 | 1.12 | 0.40 |
| 255 | 0.88 | — |
| 270 | 0.75 | — |
| 285 | 0.65 | — |
| 300 | 0.61 | 0.39 |

[1]Both sensors in the vapor phase above tap water fowing at 20 ml/min; 20°C.
[2]0.4 ml/min. of 37 wt. percent HCl slution added to tap water flow
[3]2.0 ml/min. $H_2S$ — saturated water added to tap water
[4]HCl addition stopped; tap water flow continued
[5]$H_2S$ addition stopped; tap ater flow continued

EXAMPLE 5

Utilizing the ammonium hydroxide reference electrolyte at the flow rate previously described, the two sensors were immersed in a test liquid flowing through the reactor at 67°C. Initially, the liquid passed through the reactor was deaerated tap water flowing at 20 ml/min. to which was continuously added hydrogen sulfide-saturated water (85 ppm $H_2S$) at a rate of 0.5 ml/min. After about 27 minutes, the deaerated tap water was followed by thoroughly aerated tap water containing the same amount of hydrogen sulfide. After about 45 minutes from the beginning of the test, the aerated tap water was followed by deaerated tap water containing the same amount of hydrogen sulfide. The response of the sensors to these changes is illustrated in FIG. 8. It will be observed that the change of process sensor detected the change from deaerated water to aerated water very dramatically. It is interesting to note that the electronic hydrogen sensor was much more responsive to the change back to deaerated water than was the process change sensor. Thus, it will be noted in referring to FIG. 8 that the high concentration of oxygen in the aerated water decreased the hydrogen permeation rate as indicated by the electronic hydrogen sensor, whereas in the case of near depletion of the oxygen content of the water, the hydrogen permeation rate increased sharply.

EXAMPLE 6

Using the ammonium hydroxide reference electrolyte in the operation of the process change sensor, both sensors were immersed in test liquids flowed through the reactor at about 20°C. The first flow was aerated tap water flowing at 20 ml/min. and having $H_2S$ added thereto up to 85 ppm. After about 30 minutes, the water was deaerated but the $H_2S$ content was maintained at the same level. The voltage and current values measured by the process change sensor and the electronic hydrogen sensor are set forth in Table II.

TABLE II

| Time, min. | Sensor Response | |
|---|---|---|
| | Process Change Sensor, Volts | Electronic Hydrogen Sensor, Amps ×10⁻⁶ |
| 0[1] | 0.516 | 0.470 |
| 10 | 0.515 | 0.467 |
| 20 | 0.512 | 0.464 |
| 30 | 0.512 | 0.463 |
| 40[2] | 0.511 | 0.462 |
| 43 | 0.505 | 0.461 |
| 50 | 0.520 | 0.459 |
| 60 | 0.530 | 0.458 |
| 70 | 0.535 | 0.459 |
| 80 | 0.540 | 0.461 |
| 90 | 0.550 | 0.464 |
| 100 | 0.555 | 0.467 |
| 110 | 0.550 | 0.475 |
| 120 | 0.560 | 0.477 |
| 130 | 0.555 | 0.485 |
| 140 | 0.555 | 0.491 |
| 150 | 0.555 | 0.510 |
| 160 | 0.552 | 0.515 |

[1]Both sensors in aerated tap water flowing at 20 ml/min. with 0.5 ml/min. of $H_2S$-saturated water added ($H_2S$ total concentration = 85 ppm)
[2]Water deaerated — all other conditions unchanged.

The data in Table II again shows the increase in hydrogen permeation of steel as the oxygen content of the water drops to a low level, and both sensors were able to detect small oxygen differences in the $H_2S$ corrosion system.

EXAMPLE 7

Figure 9:
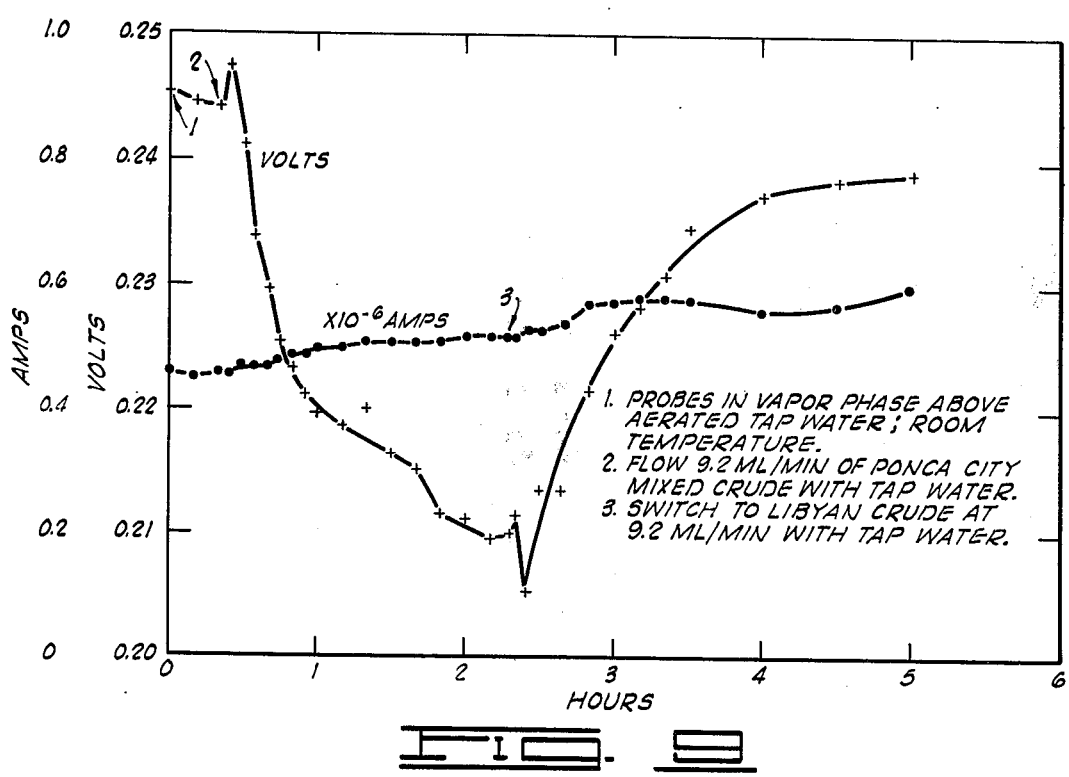

Deionized water was supplied through the internal tubing 32 to the reference and working electrodes in the process change sensor 8. Both of the sensors used in the reactor were subjected, while in the vapor phase, to a change in liquids flowing through the reactor beneath the sensors. Initially, aerated tap water was flowed through the reactor. After a period of about 20 minutes, a mixed Ponca City crude oil was flowed through the reactor behind the aerated tap water. After about 2 hours and fifteen minutes from the time of starting the test, the flow was switched to a Libyan crude oil. The flow rate of both types of crude oils through the reactor was 9.2 ml/min. The response of the sensors while in the vapor phase above the flowing liquids is shown in FIG. 9 of the drawings. It will be perceived in referring to this figure that the change from the aerated tap water to the mixed Ponca City crude oil, and then from the Ponca City crude oil to the Libyan crude oil is quite clearly reflected by the change in voltage across the electrodes in the process change sensor. The electronic hydrogen sensor, however, did not respond to the changes in liquids, indicating that the process changes occurring were not of a significant metallurgical or corrosion character within the time period of the test.

EXAMPLE 8

With the electrical circuitry shown in FIG. 4, and employing as a reference electrolyte, a 1.0 weight percent ammonium hydroxide solution delivered at a rate of 86 ml/hr. through the internal tubing 32 of the process change sensor 8, this sensor was utilized alone in the reactor shown in FIG. 2, and was located in several liquids successively passed through the reactor. Initially, Libyan crude oil was flowed through the reactor, and, after 2 hours, was followed by light gasoline. The light gasoline flow was then followed about one and one half hour later by kerosene. The response of the process change sensor to these changes in liquid flow is shown in FIG. 10.

Although certain preferred embodiments of the process change sensor of the invention have been illustrated herein, it will be understood that changes can be effected in the illustrated and described structures without departure from the basic underlying principles of the invention. For example, various other types of instrumentation can be used for providing a read-out of the process changes indicated by the process change sensor, other than the illustrated and described digital data logger. Changes and innovations of this type are therefore deemed to be circumscribed by the spirit and scope of the invention except as they may necessarily be limited by the appended claims, or reasonable equivalents thereof.

What is claimed is:
1. A process change sensor comprising:
an elongated tubing means;
open-ended housing means having one end of said tube connected to one open end thereof;
a first permeable electrode positioned in one end portion of the housing means for contacting a process medium;
a second permeable electrode positioned inwardly in the housing means from said first electrode;
electrically non-conductive fixture means positioned in said housing means and holding said electrodes in spaced relation to each other in an electrically insulated position relative to said housing means and said tubing means;
a porous body separating said first electrode from said second electrode;
means for supplying electrolyte through said tubing means to said second electrode whereby said supplied electrolyte can flow through said porous body to said first electrode, said means for supplying electrolyte to said second electrode comprising an electrolyte delivery tube within said tubing means and passageway means defined by said fixture means and extending between an end of said electrolyte delivery tube and said second electrode; and
means for measuring the change in EMF between said first and second electrodes as a result of changes in the process medium at said first electrode.

2. A process change sensor as defined in claim 1 wherein said open-ended housing means comprises:
a hollow, open-ended fitting having said tubing means connected to one open end thereof; and
a cap having an opening therethrough detachably secured on the other end of said fitting and retaining said fixture means in said fitting with said first electrode facing the opening through said cap.

3. A process change sensor as defined in claim 1 wherein each of said electrodes is a platinum electrode, and wherein said sensor further comprises:
insulated lead wires connected to each of said electrodes, extending through said tubing means, and connected to said measuring means.

4. A process change sensor as defined in claim 1 wherein said measuring means comprises:
a digital data logger device; and
an electrometer connected between the electrodes and the digital data logger device for providing a constant high impedance across the electrodes.

5. A process change sensor as defined in claim 1 wherein said porous body comprises a fritted glass plug.

* * * * *